United States Patent [19]

Whistler

[11] Patent Number: 5,073,387
[45] Date of Patent: Dec. 17, 1991

[54] METHOD FOR PREPARING REDUCED CALORIE FOODS

[75] Inventor: Roy L. Whistler, West Lafayette, Ind.

[73] Assignee: Lafayette Applied Chemistry, Inc., West Lafayette, Ind.

[21] Appl. No.: 469,153

[22] Filed: Jan. 24, 1990

[51] Int. Cl.$^5$ .............................................. A23L 1/00
[52] U.S. Cl. ........................................ 426/7; 426/44; 426/52; 426/61; 426/658; 426/661; 426/804
[58] Field of Search ................... 426/7, 44, 52, 655, 426/62, 61, 658, 661, 804

[56] References Cited

U.S. PATENT DOCUMENTS 3,399,189  8/1968  Gordon .
3,480,511  11/1969  Jones .
4,895,938  1/1990  Teraoka et al. .

FOREIGN PATENT DOCUMENTS 266101  4/1988  Japan .
266179  4/1988  Japan .

OTHER PUBLICATIONS

"Partial Enzyme Degradation of Tamarindus-Amyloid", P. Kooiman, *Nature*, No. 4578, Jul. 27, 1957, p. 201.
"The Construction of Tamarindus-Amyloid", P. Koomian, *Recueil*, No. 80 (1961), pp. 849-865.
"Enzymic Degradation of Tamarind Kernel Powder", Srivastava, et al., *Indian Journal of Technology*, vol. 8, Sep. 1970, pp. 347-349.
"Tamarind", (Chapter XVII), Rao, et al., *Industrial Gums*, R. L. Whistler & J. H. BeMiller, eds., 1973, Academic Press, pp. 369-411.
"Etude Complementaire De La Structure De Trois Galactoxyloglucanes (Amyloides) De Graines", Courtois, et al., *Carbohydrate Research*, 49, 1976, 439-449.
"Enzymatic Modification of Natural Seed Gums", Reid. et al., *Gums and Stabilizers in the Food Industry*, 4th ed., pp. 391-398.
"Action D'Une Glucanase De Penicillium Notatum Sur Les Galactoxyloglucanes", Youcef, et al., pp. 1949-1951, *Phytochemistry*, 1979, vol. 18, Pergamon Press Ltd.
"Low Viscosity Tamarind Kernel Powder-Nature and Properties", Srivastava, *Colourage*, Feb. 16, 1978, pp. 24-27.
"Production of Alpha-Xylosidase by Aspergillus Niger", Kato, et al., *J. Ferment. Technol.*, vol. 63, No. 4, pp. 389-393, 1985.

*Primary Examiner*—Marianne Cintins
*Attorney, Agent, or Firm*—Barnes & Thornburg

[57] ABSTRACT

A cellulase hydrolysate of tamarind polysaccharide is utilized as a substitute for a portion of metabolizable carbohydrates in processed foods to prepare reduced-calorie versions of said process foods having excellent organoleptic quality. The tamarind hydrolysate comprises DP 7 oligosaccharides, more typically, DP 7 and DP 9 oligosaccharides. The tamarind hydrolysate can be further processed utilizing yeast digestion and/or membrane filtration to remove monosaccharides and low DP (DP$\leq$6) oligosaccharides from the hydrolysate composition.

6 Claims, No Drawings

METHOD FOR PREPARING REDUCED CALORIE FOODS

FIELD OF THE INVENTION

This invention relates to a method for preparing processed foods having reduced calorie content. More particularly, this invention is directed to the preparation of a tamarind polysaccharide hydrolysate and its use as a multi-functional non-metabolizable food additive. The hydrolysate can be substituted at high levels not only for metabolizable carbohydrate components of processed foods, but also for a portion of fat content without adversely affecting organoleptic quality.

BACKGROUND AND SUMMARY OF THE INVENTION

Carbohydrates and fats are common constituents of processed food products. These ingredients have critical functional significance with regard to the appearance, taste, mouth feel and other organoleptic qualities of food. However, fats/oils and starch-derived carbohydrates utilized extensively in processed foods can be metabolized by the human body and thus contribute significantly to the calorie content of such foods.

In recent years consumers have become increasingly health conscious. Many individuals are attempting to minimize their intake of high-calorie foods and foods containing high levels of fat. Consumers are demanding reduced calorie and low-fat versions of traditional processed foods. Consequently there exists an expanding need for food additives which can be used as functional substitutes for the calorie-imparting contents of processed foods without adversely affecting organoleptic quality.

I have discovered that a cellulase hydrolysate of tamarind endosperm polysaccharide meets that need. The tamarind hydrolysate is unique in that unlike other carbohydrate hydrolysates it comprises 2 predominant (typically > 70%) oligosaccharides—oligosaccharides believed to have degrees of polymerization (DP) of 7 and 9, some DP 8 oligosaccharides with most of the remainder monosaccharides and DP≦6 oligosaccharides. The hydrolysate can be processed to remove monosaccharides and DP<6 oligosaccharides. The tamarind hydrolysate can be substituted at high levels for a portion of the metabolizable carbohydrate components of processed foods without compromising the organoleptic qualities of the resulting reduced calorie foods. Significantly, its use also allows reduction of the fat content of those Processed foods.

Tamarind polysaccharide is obtained from the seed of the tamarind tree, *Tamarindus indica*, a common forest and cultivated tree found primarily in India, Burma, Bangladesh and Sri Lanka. Tamarind fruit are in the form of 10-15 cm long pods consisting of about 55% pulp, about 34% seed, and about 11% shell and fiber. Tamarind seed became a commercial source of gum in 1943 when an Indian research institute discovered the gum's utility as a paper size. Since then, tamarind endosperm polysaccharide has found many commercial applications. In 1988 alone, over 800 metric tons of tamarind seed gum were exported from India.

A variety of uses for the isolated tamarind seed polysaccharide have been developed. See Rao and Srivastava, "Tamarind" in *Industrial Gums*. R. L. Whistler and J. H. Bemiller, eds., 1973, pp. 402-407. The polysaccharide has the ability to form jellies with sugar concentrates over a wide pH range. It has also been used as a stabilizer in ice creams and mayonnaise. Further, the textile industry has employed tamarind polysaccharide for sizing, finishing and printing cotton and artificial silk. In the cosmetics industry, tamarind polysaccharide has been used for preparing emulsions of essential oils, shaving creams and dentifrices. It has also found use as a binder in the manufacture of compressed pills and tablets, as an excipient in making greaseless ointments and as a gelling agent in the preparation of colloidal iodine jelly.

In accordance with the present invention, a cellulase enzyme hydrolysate of tamarind endosperm polysaccharide is utilized as a multi-functional, but non-metabolizable food additive. Further in accordance with this invention tamarind polysaccharide is converted in high yield to a food grade hydrolysate believed to comprise principally, DP 7 and DP 9 oligosaccharides using commercial cellulase. Preferably the polysaccharide hydrolysate product is processed, prior to use in accordance with this invention, to reduce the amount of oligosaccharides in the hydrolysate having a DP less than 6. In a preferred embodiment the hydrolysate is treated to remove at least a portion of the metabolizable monosaccharides produced during enzymatic hydrolysis.

Commercially available cellulases selectively hydrolyze tamarind polysaccharide to produce initially an oligosaccharide mixture comprising DP 7 and DP 9 oligosaccharides. If enzyme action is allowed to continue, the DP 9 oligosaccharide is further hydrolyzed to form a DP 7 oligosaccharide. Typically, enzymatic hydrolysis of tamarind polysaccharide in accordance with this invention is continued until the hydrolysate solution reaches a near constant viscosity (when DP 7 and DP9 oligosaccharides are the principal oligosaccharide hydrolysis products), after which time the hydrolysate solution is heated to terminate hydrolysis and to precipitate soluble proteins which then can be removed by filtration. Preferably the solution is treated to remove at least a portion of the hydrolysate oligosaccharides of DP less than 6, optionally decolorized by carbon treatment, and then freeze dried, spray dried or roll-dried to provide a multi-functional, yet non-metabolizable food additive as a free-flowing powder.

The tamarind hydrolysate can be substituted for up to 60% of the digestible carbohydrates in processed food products without adversely affecting product processing or food product organoleptic properties. Further, it has been found that when the tamarind polysaccharide is used as a carbohydrate substitute, fat content can also be reduced up to 25%. Thus use of the tamarind hydrolysate as a carbohydrate substitute in processed foods enables a significant reduction in calorie content. Significantly, too, because the hydrolysate has a more homogeneous composition (a significant percentage by weight of DP 7-DP 9 oligosaccharides) than other art-recognized carbohydrate hydrolysates, its functional performance is highly predictable in a wide variety of processed food products. Another characteristic of the tamarind polysaccharide enzymatic hydrolysate which derives from its predominant DP 7/DP 9 oligosaccharide content is that, unlike art-recognized food additive gums, the polysaccharide hydrolysate can be used at high levels in processed foods without adversely affecting the processing thereof due to elevated viscosities.

DETAILED DESCRIPTION OF THE INVENTION

In accordance with the present invention, there is provided a process for preparing a food ingredient comprising DP 7-DP 9 oligosaccharides produced by cellulase hydrolysis of tamarind polysaccharide. The product tamarind hydrolysate has been found to exhibit exceptional food-functional characteristics when used as a substitute for at least a portion of the metabolizable carbohydrate components of processed foods. Thus in another embodiment of this invention there is provided a processed food product having the tamarind hydrolysate substituted for at least a portion of its normal metabolizable carbohydrate content. Typically about 1 to about 2 parts of the hydrolysate are substituted for each part of metabolizable carbohydrate deleted from the processed food recipe.

The non-metabolizable oligosaccharide composition used in accordance with this invention is prepared by cellulase hydrolysis of polysaccharides derived from tamarind seed. Tamarind kernel powder, the ground endosperm of tamarind seed, or more specifically, tamarind seed endosperm polysaccharide is converted by cellulase enzyme action in high yield initially to an oligosaccharide mixture comprising principally two oligosaccharides, one having a degree of polymerization (DP) of 7 and the other having a DP of 9. Upon prolonged cellulase enzyme action, the DP9 oligosaccharide component is converted to the DP 7 component. The DP 7-DP 9 oligosaccharide products from cellulase hydrolysis of tamarind endosperm polysaccharide are, of course, produced in admixture with other oligosaccharides, a small percentage having DP greater than 9, but most by-product oligosaccharides having DP less than or equal to 6.

In accordance with a preferred embodiment of this invention, the enzyme hydrolysate is processed to remove at least a portion of the oligosaccharides in the hydrolysate mixture having DP less than or equal to 6. Such processing can be accomplished, for example, by membrane filtration (dialysis) or by art-recognized chromatographic separation techniques. Most monosaccharide components of the tamarind endosperm enzyme hydrolysate are removed by treating the hydrolysate mixture in solution with active yeast under conditions condusive to yeast metabolism of the monosaccharide components of the hydrolysate. Subsequent to such processing to enhance hydrolysate homogeneity, the hydrolysate composition can be isolated in solid form by freeze-drying, spray drying or roll-drying of the hydrolysate solution or by hydrolysate precipitation techniques.

Tamarind endosperm polysaccharide is commercially available in a form containing about 8% oil and in a deoiled form which contains less than about 1% oil. The deoiled form is preferred for preparation of the oligosaccharide hydrolysate in accordance with the present invention. The commercially available polysaccharide can optionally be purified by dissolution with heating in water, heating the resulting solution/suspension at 95° C. for about 30 minutes, filtering or centrifuging the solution, and finally precipitating the purified tamarind polysaccharide from the filtrate with ethanol.

The exact composition of tamarind endosperm polysaccharide is not fully known. Early work indicated glucosyl, xylosyl and galactosyl units in the structure. The ratio of glucosyl:xylosyl:galactosyl units in the polysaccharide has been reported as 3:2:1 by a number of workers and as 4:3:1-1.5 by others. Analysis by methylation and hydrolysis of the permethylated polysaccharide suggests a highly branched chain with non-reducing ends consisting of D-galactopyranosyl and L-arabinofuranosyl units. Periodate oxidation of each sugar unit indicates the absence of (1–3) linkages. It has been suggested that the main chain is cellulose with frequent branching with short side chains consisting of one or two D-xylopyranosyl units capped with D-xylopyranosyl, D-galactopyranosyl or L-arabinofuranosyl units.

Conversion of tamarind endosperm polysaccharide to a hydrolysate comprising predominately DP 7-DP9 oligosaccharides is accomplished by action of a cellulase selected from cellulases of fungal and bacterial origin. The enzymatic hydrolysis can be accomplished in aqueous solution containing tamarind polysaccharide over a wide range of polysaccharide concentrations. Thus, the reaction can be accomplished by dissolving tamarind polysaccharide in aqueous solution at a concentration from about 1% by weight up to a concentration limited only by polysaccharide solubility and solution viscosity. Indeed, tamarind polysaccharide can be added periodically to an ongoing cellulase hydrolysis reaction mixture to attain carbohydrate concentrations in the hydrolysate as high as 50 weight percent.

The cellulase can be selected from any of a wide variety of commercially available cellulases of fungal or bacterial origin. Suitable cellulases include those produced by *Aspergillus niger*, *Trichoderma reesei*, *Penicillium notatum*, *Myrothecium verrucaria*, *Aspergillus flavus*, *Aspergillus oryzae*. Preferred cellulases are those derived from Aspergillus species and Trichoderma species. Commercial cellulases from different sources/organisms have been found to exhibit some differences in rate of hydrolysis and to some extent in the ratio of oligosaccharides produced by their action on tamarind polysaccharide. Thus, to optimize production of the polysaccharide hydrolysate useful in accordance with this invention, it is preferable that each enzyme lot be evaluated in laboratory test runs for their cellulytic activity on a tamarind polysaccharide substrate and that such information be used to optimize conditions for the larger scale production of tamarind hydrolysate. Commercially available cellulase isolates from *Aspergillus niger* (Biocellulase A concentrate, from Biocon, Inc., Lexington, Ky.) and from *Trichoderma reesei* (Rohament CT. from Rhom Tech., Inc., Malden, Mass.) have been found to be the most preferred cellulases for use in production of the oligosaccharide containing polysaccharide hydrolysates for use in accordance with this invention.

The amount of enzyme to be used to effect the requisite hydrolysis of tamarind polysaccharide depends somewhat on reaction conditions and the activity level of the cellulase. Under optimum conditions, the enzyme can be used at levels as low as 0.05 percent weight relative to the weight of tamarind polysaccharides starting material. Typically the amount of cellulase appropriate for production of the hydroysate will range from about 0.1% to about 5% of the weight of the tamarind polysaccharide starting material. The time for accomplishing the hydrolysis reaction likewise will vary depending on the cellulase hydrolysis conditions. Typical temperatures range from about 30 to about 50° C., more preferably between about 35° and 45° C. Under conditions detailed for optimum activity of the particular cellulase being used, typically detailed by the enzyme manufacturer in product literature, the hydrolysis reaction is completed in a period of about 1 to about 12 hours, more typically in about 4 to about 8 hours. The progress of the polysaccharide hydrolysis reaction can be monitored by standard analytical techniques such as thin layer chromatography, gel permeation chromatography or high pressure liquid chromatography.

The tamarind polysaccharide is hydrolyzed during cellulase hydrolysis to yield a low viscosity product comprising, predominantly, two oligosaccharides of DP 7 and DP9. Continuing the cellulase hydrolysis reaction results in reduction of the amount of DP9 oligosaccharide and increased amounts of the DP 7 oligosaccharide, presumably by direct cellulytic hydrolysis of the DP9 oligosaccharide product. Under typical enzymatic hydrolysis conditions at least 80% by weight of deoiled tamarind polysaccharides starting material is converted to tamarind hydrolysate of which about 70% to about 80% by weight is a mixture of the DP 7-DP 9 oligosaccharides. The remaining portion of the crude hydrolysate consists essentially of monosaccharides and low molecular weight (DP less than 6) oligosaccharides.

The product hydrolysate comprising DP 7/DP9 oligosaccharides is isolated from the hydrolysis reaction mixture by precipitation or solution drying techniques. Protein components in the hydrolysis medium can be separated, by heating the reaction mixture to a temperature of at least 90° C., preferably between about 95° C. and 100° C. and thereafter filtering the hydrolysate solution. The heating step effects denaturation and precipitation of the protein from solution. Remaining soluble proteins in the filtrate can be removed by contacting the filtrate with any commercially available ion exchange resin. This can be accomplished, for example, either by slurrying the hydrolysate solution with the resin and filtering or by passing the hydrolysate solution through a column packed with the ion-exchange resin.

Another step for processing the hydrolysate solution which is desirable but not always necessary is treatment of the hydrolysate solution with activated carbon. Such is accomplished by adding activated carbon (charcoal), usually in an amount equal to about 5 to about 20% of the weight of the dissolved hydrolysate, to the hydrolysate solution, heating the solution and thereafter filtering, preferably with use of a filter aid such as celite. Such treatment is effective to decolorize the hydrolysate solution and to reduce the concentration of organic impurities.

The crude carbohydrate hydrolysate can be isolated from the processed hydrolysate solution by solution drying techniques, preferably lyophilization, or by precipitation with ethanol. Preferably, however, the tamarind hydrolysate solution is further processed to remove at least a portion of the monosaccharides and lower molecular weight oligosaccharides (DP less than 6). Because the principle use of the product tamarind hydrolysate composition is as a substitute for metabolizable carbohydrates in processed foods to reduce calorie content, it is desirable to minimize the level of metabolizable monosaccharides in the hydrolysate composition. Further there is evidence in the literature that DP2-DP6 oligosaccharides tend to induce intestinal dysfunction in some people. Thus, it is preferred that the levels of monosaccharides and DP≦6 oligosaccharides are reduced as much as possible in the hydrolysate product. This can be accomplished by membrane filtration or dialysis using commercially available membranes of controlled pore size. Monosaccharide content of the crude hydrolysate can be reduced, as well, by using the crude hydrolysate as a medium for yeast fermentation. Metabolizable monosaccharides in the hydrolysate solution are digested by the growing yeast. Following the yeast digestion processing step, the yeast cells can be removed from the hydrolysate solution by centrifugation or other art-recognized cell-separation techniques. As in the case of the cellulase hydrolysis of the tamarind polysaccharide, the progress of yeast digestion can be followed by standard analytical techniques.

Following the hydrolysate solution processing, again which can optionally include membrane filtration, decolorization and/or sterilization, the product oligosaccharides can be isolated from the hydrolysate solution using standard carbohydrate isolation techniques such as lyophilization or precipitation. Selective ethanol precipitation of the hydrolysate oligosaccharides can be used to provide a hydrolysate product consisting essentially of DP 7-DP9 oligosaccharides without use of the above-mentioned membrane filtration/yeast processing steps. The higher molecular weight oligosaccharides, being less soluble, can be preferentially precipitated leaving more of the lower molecular weight oligosaccharides (DP≦6) in solution.

The product oligosaccharide mixture is typically isolated as a dry, free flowing, white to cream colored powdered. Alternatively, the processed hydrolysate solution can itself be used as a food additive as a means for introducing the oligosaccharide mixture into processed food recipes.

The tamarind polysaccharide hydrolysate can be used, in accordance with this invention, as a functional substitute for the metabolizable carbohydrate content of processed foods to provide reduced-calorie processed food products. It has been found that a composition comprising DP 7-DP9 oligosaccharides derived by cellulase hydrolysis of tamarind polysaccharides can be substituted for as much as 60% of the metabolizable carbohydrates in processed food without adversely affecting organoleptic quality of the modified food products. Moreover, the use of such oligosaccharide composition in processed foods allows, as well, a reduction in fat content without noticeable affect on food quality. More particularly, I have found that when the tamarind hydrolysate (DP 7-DP9 oligosaccharides) is substituted for about 10 to about 40% of the carbohydrates in a processed food composition, fat content can be reduced as much as 25%.

The tamarind derived oligosaccharide composition can be used in accordance with this invention to produce reduced calorie candy, chewing gum, dry cake and cookie mixes, frozen dairy desserts, nutritional bars, gelatin desserts, baked goods and spoonable dressings. Further, it may be employed as a bulking agent without significant increase in batter/product viscosity. The composition has been found to dissolve quickly in water to give clear solutions. It can be used as a non-caloric carrier for synthetic sweeteners. When mixed with synthetic sweetener and added either to ice tea or hot coffee, the dissolution of the product is instantaneous. It has been noted as well that the tamarind hydrolysate oligosaccharide composition can act as a sweetness intensifier. A baked cookie of high quality can be prepared by substituting the hydrolysate for about 10 to about 40% of the sugar called for on the original cookie recipe. In another application of the oligosaccharide composition in accordance with the invention, the composition is combined with dry milk solids to produce a coffee whitener.

EXAMPLE 1

Deoiled commercial tamarind seed powder was sifted into water with vigorous stirring to form a 3% by weight solution/suspension. The solution was heated to 90°-95° C. for a 30 minute period with vigorous stirring and then cooled to 40° C. before commercial cellulase enzyme (3% by weight of tamarind powder) from *Aspergillus niger* (Biocellulase A Concentrate from Biocon, Inc.) is added. The reaction was allowed to proceed with stirring at 40° C. for about 16 hours.

The progress of the cellulase hydrolysis reaction was followed by taking aliquots from the reaction mixture after 2, 4, 5 and 16 hours, deactivating the enzyme by heating those samples and utilizing HPLC analysis to determine the relative amounts of oligosaccharides present having DP greater than 9, DP equal to 9, DP equal to 7, DP equal to 1. The results of such analyses are shown in Table I below. The data indicate that the hydrolysis reaction utilizing Biocellulase A converted the tamarind polysaccharides to the principle DP9 and PD7 oligosaccharide products after 4 hours. Continued hydrolysis provided further reduction of DP greater than 9 oligosaccharides and DP9 oligosaccharide with concomitant increase in concentration of the DP 7 oligosaccharide product.

TABLE I

HYDROLYSIS OF DEOILED TAMARIND POWER
(With Biocellulase A Concentrate)
Percent Hydrolysis

| Component Present | After 2 hours | After 4 hours | After 5 hours | After 16 hours |
|---|---|---|---|---|
| DP >9 | 16 | 1 | 0.4 | 0.2 |
| DP 9 | 32 | 25 | 13 | 2 |
| DP 7 | 45 | 58 | 73+ | 76+ |
| DP 1 | 2 | 3.6 | 3 | 6 |

The reaction mixture was then heated to 95°-100° C. for 10 minutes to inactivate the enzyme and to precipitate at least a portion of the protein present in the resulting tamarind hydrolysate solution. The aqueous hydrolysate was then cooled to 60° C. and filtered through a Celite pad to remove the protein precipitate. The filtrate was treated with activated carbon (3-6% by weight of the tamarind powder) to decolorize the solution and remove organic impurities. Lyophilization of the decolorized hydrolysate solution provided the tamarind hydrolysate comprising DP 7 and DP 9 oligosaccharides as a white powder. The viscosity of a 2% aqueous solution of the product was about 1.5 centipoises when measured in an Ostwald Viscometer at 25° C.

EXAMPLE 2

The procedure described in Example 1 was repeated using Rohament CT brand cellulase in place of Biocellulase A brand cellulase. The reaction was terminated after seven hours. Table II summarizes the progress of that reaction after 5 and 7 hours.

TABLE II

HYDROLYSIS OF DEOILED TAMARIND POWDER
(With Rohament CT Cellulase)
Percent Hydrolysis

| Component Present | After 5 Hours | After 7 Hours |
|---|---|---|
| DP >9 | 7 | 0.4 |
| DP 9 | 32 | 27 |
| DP 7 | 54 | 58 |
| DP 1 | 2 | 2 |

The viscosity of a 2% aqueous solution of the hydrolysate product is about 2 when measured in an Ostwald Viscometer at 25° C.

EXAMPLE 3

A portion of the dried tamarind hydrolysate obtained in accordance with Example 1 is dissolved in water and introduced into a membrane filtration apparatus utilizing a membrane having a pore size selected to allow passage of molecules having a molecular weight of less than 1000. Ethanol precipitation of the hydrolysate solution after membrane filtration processing provides a composition consisting essentially of DP 7 and DP 9 oligosaccharides substantially free of monosaccharides and oligosaccharides having a degree of polymerization of less than 6.

EXAMPLE 4

Following the general procedure described in Example 1, a 50 gram sample of tamarind endosperm polysaccharide is hydrolyzed at 40° C. for 6 hours in 1500 ml of water using 2.0 grams of Biocellulase A Concentrate (from Biocon, Inc., Lexington, Ky.) cellulase enzyme. Using 1.76 gram portions of the resulting freeze-dried tamarind polysaccharide hydrolysate dissolved in 10 ml portions of water at pH 5.7, several yeast digestion conditions were evaluated for effectiveness for reducing monosaccharide content of the hydrolysate. The hydrolysate solutions were heated either to 30° or 40° or 50° C. in a water bath. Yeast (Fleschmann's Active Dry Yeast), 0.70 grams or 0.106 grams, was added and the resulting mixture was stirred for 24 hours or 48 hours at 30°, 40° or 50°. Each reaction mixture was then boiled 10 minutes to deactivate the yeast. Insolubles were removed by adding Celite to the mixture and filtering through a pad of Celite on Whatman No. 1 filter paper. The oligosaccharide product was recovered by freeze-drying the filtrate.

Reduction of monosaccharides by yeast digestion was quantitated by HPLC analysis. A small amount of each yeast treated tamarind hydrolysate was passed through a column of Amberlite 120 cation exchange resin to remove remaining soluble protein. The filtrate was concentrated under reduced pressure and chromatographed on an Aminex HPX87P monosaccharide HPLC column operated at 60° C. with a water elutent flow rate of 0.5 ml/min. A Varian RI detector was used with a Varian 5000 HPLC pump. The results of the HPLC analysis for the respective yeast digestions are summarized in Table III.

TABLE III

MONOSACCHARIDE COMPOSITION OF TAMARIND OLIGOSACCHARIDE MIXTURE (TOM) AND YEAST DIGESTED TOM

| Treatment Conditions | | | Monosaccharide Content | | | |
|---|---|---|---|---|---|---|
| Temp. (°C.) | Time (hr.) | Yeast (%) | Glc (%) | Xyl (%) | Gal (%) | Ara (%) |
| No treatment | | | 2.4 | 0.7 | 1.7 | 0.8 |
| 30 | 24 | 4 | 0.2 | 0.7 | — | 0.4 |
| 30 | 48 | 4 | 0.1 | 0.8 | — | — |
| 40 | 24 | 4 | 0.1 | 0.8 | — | 0.2 |
| 40 | 24 | 6 | 0.1 | 0.8 | — | — |
| 50 | 7 | 4 | — | 0.6 | 1.8 | 0.8 |
| 50 | 24 | 4 | 0.2 | 0.7 | 1.7 | 0.8 |
| 50 | 48 | 4 | 0.1 | 0.7 | — | — |

Tamarind polysaccharide hydrolysate produced by cellulase hydrolysis of tamarind polysaccharide contained 2.4% D-glucose, 0.7% xylose, 1.7% D-galactose and 0.8% L-arabinose as measured by HPLC. Treatment of the tamarind hydrolysate with 4% by weight of yeast for 24 hours at 30° C. reduced D-glucose to 0.2%, L-arabinose to 0.4%, and removed all D-galactose. Continuing the reaction for 48 hours at 30° C. removed the remaining L-arabinose. HPLC indicated a small peak, 0.1% of the product, which appeared at the same retention time as D-glucose. It is believed that the small peak is likely that of an impurity because the yeast is expected to completely digest D-glucose. The experiment indicated that the most preferred conditions, i.e. those that were most effective to reduce monosaccharide content, were with use of 6% by weight yeast for 24 hours, at 40° C. Yeast digestion under those conditions removes all monosaccharides except xylose from the tamarind oligosaccharide mixture.

EXAMPLE 5

Two procedures are presented for enzymatic hydrolysis of deoiled tamarind polysaccharide to oligosaccharides with less than 1-2% polysaccharide. Yield of hydrolysate is about 80% of the tamarind gum. The hydrolysate contains 70% or more of DP 7 and 9 oligosaccharides, with 9-10% of DP 8, about 10% monosaccharides, and up to 10% of DP 2 to DP 6 oligosaccharides.

MATERIALS

Materials used were deoiled tamarind seed polysaccharide, Biocellulase A Concentrate enzyme, Dowex G-60 activated carbon (Aldrich Chemical co. and Celite 521 (Aldrich Chemical Co.)

GENERAL PROCEDURES

A. Enzymatic Hydrolysis Of A 20% Tamarind Dispersion ("One-Pot" Process).

Tamarind is sifted into an enzyme and water solution at 50° C. with vigorous stirring over 15 minutes in an amount to give a 20% tamarind dispersion with an amount of Biocellulase A Concentrate enzyme equal to 1% of tamarind weight. After completion of tamarind addition, the mixture is stirred an additional 20 minutes at 50° C. Over the next 15 minutes, the temperature is brought from 50° C. to 70° C. Upon reaching 70° C., the dispersion becomes viscous, but slow stirring is continued another 20 minutes at 70° C. to completely hydrate the gum. Dispersion temperature is lowered to 50° C. and additional enzyme equal to 3% of tamarind weight is added. Hydrolysis at 50° C., with stirring, is continued for 4 hours. To deactivate enzyme after hydrolysis completion, and to precipitate protein, the mixture is boiled 10 minutes.

After cooling to near 50° C., the insolubles are removed by adding Celite to the mixture and filtering through Celite. Filtration is easiest if a small portion of the mixture is added to the Celite and allowed to filter through before more is added. Thus, layers of Celite and insolubles are deposited, preventing a buildup of slimy proteinaceous material which greatly slows filtration. Celite is washed with fresh water and filtered again to fully recover hydrolysate.

Yellow color of tamarind hydrolysate is greatly reduced with activated carbon decolorization. To the hydrolysate is added 10% activated carbon, w/w tamarind, and mixture is stirred at 50° C. for 2 hours. Carbon is removed by adding Celite to the mixture and filtering through a thick pad of Celite. to recover hydrolysate absorbed on the Celite, the top carbon layer is scraped off and the Celite washed with fresh water and filtered through a thin Celite pad.

Yield of hydrolysate (by lyophilization) is approximately 80%. The product from a hydrolysis reaction using 5 lbs of tamarind polysaccharide has a viscosity of 1 centipoise at 2% by weight in water at 25° C.

HPLC RESULTS

Hydrolysis was conducted for various time periods to determine at what point tamarind polysaccharide was reduced to oligosaccharides. As shown in Table IV, 4 hours after adding enzyme nearly all high molecular weight material was converted to oligosaccharides. Longer hydrolysis times converts DP 9 oligomer into DP 7 and slightly increases monosaccharide amount. Thus, a hydrolysis time of 4 hours is recommended.

TABLE IV

HPLC RESULTS FROM "ONE-POT" HYDROLYSIS
Percent Of Hydrolysate

| Fraction | 3 Hours Hydrolysis | 4 Hours Hydrolysis | 5 Hours Hydrolysis | 6 Hours* Hydrolysis |
|---|---|---|---|---|
| High MW | 5.5 | 1.1 | 0.8 | 0.8 |
| ~DP 9 | 30.7 | 24.1 | 18.8 | 15.5 |
| ~DP 7 | 43.6 | 46.8 | 50.0 | 51.3 |
| Monosaccharide | 7.4 | 9.8 | 10.2 | 10.9 |

*Hydrolysis time remaining time after 3% by weight enzyme addition. Remaining hydrolysate not included in Table IV is DP 2–DP 6 and DP 8 oligosaccharides.

B. Enzymatic Hydrolysis Of A 20% Tamarind Dispersion ("Two-Pot" Procedure).

Tamarind is sifted into vigorously stirred water at 25° C. to give a 25% dispersion. The temperature is brought to 95° C. and the dispersion is allowed to stand 30 minutes at 95° C., after which temperature is reduced to 50° C. or below. In a separate container, water equal to one-third the amount used to make the 25% dispersion is brought to 50° C. and enzyme equal to 3% of the tamarind weight is added with slow stirring. Following dissolution of the enzyme, the thick, putty-like hydrated tamarind is scooped into the enzyme solution with vigorous mechanical stirring to assist in dispersing and breaking up clumps. Addition of all tamarind requires about 20 minutes and hydrolysis at 50° C. is continued 4 hours after tamarind is dispersed in enzyme solution.

Following hydrolysis completion, enzyme is denatured and the protein precipitated by boiling 10 minutes.

Filtration of insolubles with Celite and decolorizing with activated carbon is as described above.

HPLC RESULTS

Enzymatic hydrolysis was conducted for various time periods to determine length of time necessary to convert polysaccharide into oligosaccharides, predominantly DP 9 and 7. As shown in Table V, a hydrolysis time of 4 hours was required to lower molecular weight to oligosaccharide level.

TABLE V

HPLC RESULTS FROM "TWO-POT" HYDROLYSIS
Percent of Hydrolysate

| Fraction | 2 Hours Hydrolysis | 3 Hours Hydrolysis | 4 Hours Hydrolysis | 5 Hours Hydrolysis | 6 Hours* Hydrolysis |
|---|---|---|---|---|---|
| High MW | 24.1 | 9.5 | — | — | 0.26 |
| DP 9 | 28.5 | 30.8 | 28.5 | 21.1 | 13.7 |
| DP 7 | 27.5 | 36.8 | 46.1 | 51.2 | 55.4 |
| Monosaccharide | 7.5 | 8.3 | 9.3 | 9.8 | 8.4 |

*Remaining percentage of hydrolysate is DP 2-DP 6 and DP 8 oligosaccharides.

EXAMPLE 6

Tamarind hydrolysate prepared in accordance with Example 1 is substituted for portions of the flour and sugar ingredients in a brownie recipe thereby reducing the calorie content of the baked product by about 34%: The modified brownie recipe is as follows:
- 140 g: Granulated sugar
- 100 g: Tamarind hydrolysate
- 2 g: Salt
- 2.8 g: Baking soda
- 100 g: Bread flour
- 45 g: Cellulose fiber
- 27 g: Dutch cocoa
- 0.5 g: Xanthan gum
- 56 g: All purpose shortening
- 0.4 g: Flavoring
- 48 g: Liquid whole eggs
- 125 g: Water Procedure: Combine granulated sugar and cocoa; add shortening, and mix. Stir in whole eggs and add tamarind hydrolysate, salt, baking soda, flour, cellulose fiber, xanthan gum and mix. Add flour and water and beat until smooth. Spread batter in a greased pan and bake at 350° F. until sides begin to pull away from edge of pan.

The flavor and texture of brownies prepared using the tamarind hydrolysate modified recipe are comparable in taste, appearance and texture to brownies prepared utilizing the unmodified brownie recipe.

EXAMPLE 7

Tamarind hydrolysate is used to replace about one-half of the sugar in a lemon-flavored hard candy recipe reducing the candy's calorie content by about 50%. The modified recipe for this confection is as follows:
- 49.0%: Tamarind hydrolysate
- 49.0%: Sucrose
- 0.9%: Sodium citrate
- 0.9%: Citric acid
- 0.15%: Lemon flavor
- 0.05%: F D & C color number 6, 10% solution Water (amount sufficient to dissolve ingredients)

Procedure: Bring water to boil in large, heavy pan; remove from heat. Add tamarind oligosaccharide and sucrose and stir until dissolved. Return to heat and when mixture begins to boil, cover and cook for about 3 minutes. Uncover, and cook at high heat without stirring until temperature of candy mixture reaches about 310° F. Remove to low heat and stir in remaining ingredients. Pour candy onto slab or into molds. Brush with butter or oil.

The reduced calorie candy has a flavor and mouth feel comparable to candy prepared using the unmodified recipe.

EXAMPLE 8

Tamarind hydrolysate is used in the preparation of a reduced calorie yellow cake as follows:
- 2 eggs
- 1 cup milk
- ⅔ cup soft shortening
- 2¼ cups shifted cake flour
- 1 cup granulated sugar
- 1 cup Tamarind oligosaccharide
- 3 tsp. double-acting baking powder
- 1 tsp. salt
- 1 tsp. vanilla extract Into large bowl, sift flour, tamarind oligosaccahride, sugar, baking powder and salt. Drop in shortening, then pour in ⅔ cup milk and vanilla. Beat with electric mixer at medium speed for 2 minutes. beat with spoon in 300 sweeping round-the-bowl strokes, or 2 minutes by clock, rotating bowl and scraping it often.

Add ⅓ cup milk and the eggs, unbeaten, and beat with mixer at medium speed 2 minutes or with spoon 300 strokes—2 minutes. Pour batter into 2 layer pans, dividing equally. Bake at 375° F. 25 to 30 minutes, or until they spring back when touched lightly in center.

The resulting reduced calorie yellow cake is organoleptically indistinguishable from the unmodified yellow cake recipe.

EXAMPLE 9

Tamarind hydrolysate is used as a substitute for a portion of the sugar in a chocolate pudding mix as follows:
- 6.5%: Sugar
- 0.03%: Sodium stearoyl-2-lactylate
- 3.7%: Tamarind Oligosaccharide
- 0.47%: Sodium pyrophosphate
- 0.67%: Calcium gluconate
- 0.08%: Salt
- 3.80%: Modified starch
- 1.80%: Dutch cocoa
- 83.2%: Skimmed milk Procedure: Blend together all ingredients except the skimmed milk. Stir in milk and mix at low speed until well blended. Pour into dish and refrigerate for at least one hour.

The instant pudding prepared in accordance with the tamarind hydrolysate modified recipe has a taste, viscosity and mouth feel comparable to the pudding prepared utilizing the unmodified recipe.

EXAMPLE 10

An artificial sweetener composition is prepared by blending the following ingredients:

3.5 g: Calcium saccharin
1000 g: Tamarind hydrolysate
2 g: Cream of tartar
2 g: Calcium silicate.

Each 1 gram portion of the resulting free-flowing powder mixture has the sweetness of two (2) teaspoons of sugar. It dissolves instantly upon addition to hot or cold water.

I claim:

1. In a method for modifying a food product containing carbohydrates and fat to have reduced calorie content by substituting non-digestible components for at least a portion of its digestible carbohydrate components, the improvement which comprises substituting a first portion of a cellulase hydrolysate of tamarind polysaccharide for a second portion of a digestible carbohydrate component of said food product.

2. The improvement of claim 1 wherein the tamarind polysaccharide cellulase hydrolysate comprises DP 7 and DP 9 oligosaccharides.

3. The improved method of claim 1 wherein the tamarind polysaccharides cellulase hydrolysate is also substituted for at least a portion of the fat content of said food product.

4. A modified food product prepared in accordance with the improvement of claim 1.

5. A food product having an ingredient composition modified to reduce its calorie content relative to that of its unmodified ingredient composition comprising digestible carbohydrates, the modified product ingredient composition of said food product comprising a first portion of a cellulase hydrolysate of tamarind polysaccharide as a substitute for a second portion of the digestible carbohydrates in the unmodified ingredient composition.

6. The food product of claim 5 wherein the modified product ingredient composition of said food product comprises DP 7 and DP 9 oligosaccharides derived by cellulase hydrolysis of tamarind polysaccharide.

* * * * *